(12) United States Patent
Vahabzadeh-Hagh et al.

(10) Patent No.: US 12,318,089 B2
(45) Date of Patent: Jun. 3, 2025

(54) ENDOSCOPIC STAPLER AND STAPLE REMOVER

(71) Applicants: The Regents of the University of California, Oakland, CA (US); Andrew Vahabzadeh-Hagh, La Jolla, CA (US); Rebeca Cardenas, Santa Ana, CA (US); Anne Edquilang, San Diego, CA (US); Wei Te Ha, West Covina, CA (US); Adam Lin, San Jose, CA (US)

(72) Inventors: Andrew Vahabzadeh-Hagh, La Jolla, CA (US); Rebeca Cardenas, Santa Ana, CA (US); Anne Edquilang, San Diego, CA (US); Wei Te Ha, West Covina, CA (US); Adam Lin, San Jose, CA (US)

( * ) Notice: Subject to any disclaimer, the term of this patent is extended or adjusted under 35 U.S.C. 154(b) by 44 days.

(21) Appl. No.: 18/001,164

(22) PCT Filed: Jun. 10, 2021

(86) PCT No.: PCT/US2021/036892
§ 371 (c)(1),
(2) Date: Dec. 8, 2022

(87) PCT Pub. No.: WO2021/252817
PCT Pub. Date: Dec. 16, 2021

(65) Prior Publication Data
US 2023/0210529 A1  Jul. 6, 2023

Related U.S. Application Data

(60) Provisional application No. 63/037,517, filed on Jun. 10, 2020.

(51) Int. Cl.
*A61B 17/10* (2006.01)
*A61B 17/00* (2006.01)
*A61B 17/076* (2006.01)

(52) U.S. Cl.
CPC ........ *A61B 17/10* (2013.01); *A61B 17/00234* (2013.01); *A61B 17/076* (2013.01)

(58) Field of Classification Search
CPC . A61B 17/10; A61B 17/00234; A61B 17/076; A61B 17/064
(Continued)

(56) References Cited

U.S. PATENT DOCUMENTS

| 4,556,058 | A | * | 12/1985 | Green | A61B 17/128 606/174 |
| 4,576,165 | A | * | 3/1986 | Green | A61B 17/128 606/143 |

(Continued)

OTHER PUBLICATIONS

ISA, International Search Report & Written Opinion for International Application No. PCT/US2021/036892. Mail Date: Sep. 2, 2021. 15 pages.

*Primary Examiner* — Dariush Seif
(74) *Attorney, Agent, or Firm* — Perkins Coie LLP

(57) ABSTRACT

Disclosed is an endoscopic stapler that can be operated through the small working channel of a laryngoscope, other rigid endoscope, or a natural orifice to safely and effectively connect tissues permanently or semi-permanently. The endoscopic stapler apparatus includes a handle including a trigger, an outer shaft coupled to the handle, and an inner shaft with prongs positioned at a distal end of the inner shaft. The endoscopic stapler further includes a hook, wherein the hook and prongs are positioned to capture a staple at a tip of the prongs, wherein a proximal end of the inner shaft is coupled to the trigger, and wherein activation of the trigger causes the prongs to translate away from the handle causing the prongs to bend and close the staple.

23 Claims, 17 Drawing Sheets

(58) Field of Classification Search
USPC .................................................. 227/175.1
See application file for complete search history.

(56) References Cited

U.S. PATENT DOCUMENTS

| | | | | |
|---|---|---|---|---|
| 4,624,254 | A * | 11/1986 | McGarry | A61B 17/128 606/143 |
| 4,802,478 | A * | 2/1989 | Powell | A61B 17/0684 606/142 |
| 5,089,009 | A * | 2/1992 | Green | A61B 17/064 606/220 |
| 5,171,249 | A * | 12/1992 | Stefanchik | A61B 17/1285 606/143 |
| 5,334,196 | A * | 8/1994 | Scott | A61B 17/076 254/28 |
| 5,337,937 | A * | 8/1994 | Remiszewski | A61B 17/105 227/19 |
| 5,356,064 | A | 10/1994 | Green et al. | |
| 5,364,002 | A | 11/1994 | Green et al. | |
| 5,366,479 | A | 11/1994 | Mcgarry et al. | |
| 5,383,881 | A * | 1/1995 | Green | A61B 17/1285 606/143 |
| 5,403,326 | A * | 4/1995 | Harrison | A61B 17/10 227/181.1 |
| 5,413,272 | A | 5/1995 | Green et al. | |
| 5,425,489 | A * | 6/1995 | Shichman | A61B 17/0643 606/220 |
| 5,431,323 | A | 7/1995 | Smith et al. | |
| 5,497,933 | A * | 3/1996 | DeFonzo | A61B 17/0684 227/176.1 |
| 5,560,532 | A * | 10/1996 | DeFonzo | A61B 17/0684 227/176.1 |
| 5,562,681 | A * | 10/1996 | Crainich | A61B 17/076 606/138 |
| 5,591,178 | A * | 1/1997 | Green | A61B 17/1285 606/139 |
| 5,720,756 | A * | 2/1998 | Green | A61B 17/1285 606/139 |
| RE36,720 | E * | 5/2000 | Green | F16B 2/22 606/151 |
| 6,059,799 | A * | 5/2000 | Aranyi | A61B 17/1285 606/143 |
| 6,129,740 | A * | 10/2000 | Michelson | A61B 17/2909 606/174 |
| 7,648,514 | B1 * | 1/2010 | Nakao | A61B 17/064 606/151 |
| 7,866,526 | B2 | 1/2011 | Green et al. | |
| 8,241,303 | B2 * | 8/2012 | Sinnreich | A61B 17/076 606/138 |
| 9,011,464 | B2 * | 4/2015 | Zammataro | A61B 17/1285 606/157 |
| 9,307,985 | B2 * | 4/2016 | Vold | A61F 9/007 |
| 9,713,474 | B2 | 7/2017 | Lorenz | |
| 10,010,321 | B2 * | 7/2018 | Cocaign | A61B 17/0682 |
| 10,085,747 | B2 * | 10/2018 | Peterson | A61B 17/0682 |
| 10,945,725 | B2 * | 3/2021 | Hollis | A61B 17/0642 |
| 11,147,557 | B1 * | 10/2021 | Butch | A61B 17/083 |
| 2003/0233142 | A1 * | 12/2003 | Morales | A61B 8/12 623/2.37 |
| 2005/0216036 | A1 | 9/2005 | Nakao | |
| 2005/0274768 | A1 * | 12/2005 | Cummins | A61B 17/0644 227/175.1 |
| 2006/0079913 | A1 * | 4/2006 | Whitfield | A61B 17/0682 606/142 |
| 2008/0078806 | A1 | 4/2008 | Omaits et al. | |
| 2010/0274263 | A1 * | 10/2010 | Disch | A61B 17/1285 606/142 |
| 2011/0087241 | A1 * | 4/2011 | Nguyen | A61B 17/1285 606/142 |
| 2011/0087243 | A1 * | 4/2011 | Nguyen | A61B 17/1285 606/143 |
| 2012/0197269 | A1 * | 8/2012 | Zammataro | A61B 17/10 606/142 |
| 2014/0005694 | A1 * | 1/2014 | Shelton, IV | A61B 34/30 606/143 |
| 2014/0074143 | A1 * | 3/2014 | Fitzgerald | A61B 17/10 606/199 |
| 2015/0245841 | A1 * | 9/2015 | Linder | A61B 17/068 606/151 |
| 2015/0305740 | A1 * | 10/2015 | Peterson | A61B 17/0682 606/216 |
| 2019/0008514 | A1 * | 1/2019 | Vasta | A61B 17/0642 |
| 2019/0046206 | A1 * | 2/2019 | Stokes | A61B 17/068 |
| 2019/0125359 | A1 * | 5/2019 | Shelton, IV | A61B 17/1222 |
| 2019/0125360 | A1 * | 5/2019 | Shelton, IV | A61B 17/3417 |
| 2019/0150921 | A1 * | 5/2019 | Fonte | A61B 17/0684 |
| 2019/0239970 | A1 * | 8/2019 | Stokes | A61B 34/37 |
| 2019/0247048 | A1 * | 8/2019 | Gasparovich | A61B 34/71 |
| 2020/0129178 | A1 * | 4/2020 | Stokes | A61B 34/37 |
| 2020/0253604 | A1 * | 8/2020 | Westling | A61B 17/0682 |
| 2023/0210529 | A1 * | 7/2023 | Vahabzadeh-Hagh | A61B 17/076 227/175.1 |

\* cited by examiner

ENDOSCOPIC STAPLER AND STAPLE REMOVER

CROSS-REFERENCE TO RELATED APPLICATIONS

This patent document is a U.S. National Stage of International Application No. PCT/US2021/036892, which claims priority to, and benefits of, U.S. Provisional Patent Application No. 63/037,517 entitled "ENDOSCOPIC STAPLER" filed on Jun. 10, 2020. The content of the aforementioned patent application are incorporated by reference in their entireties as part of the disclosure of this patent document.

TECHNICAL FIELD

This patent document relates to medical staplers and staple removers, and in particular staplers and staple removers for use with endoscopic equipment.

BACKGROUND

Recent improvements in endoscopy have improved the ability of physicians to access and treat the larynx, trachea, and/or esophagus of a patient. New tools including lasers have been used to cut tissue. However, connecting/repairing tissue which is currently performed via sewing sutures is cumbersome, slow and often inaccurate. New medical tools are needed to connect tissue in restricted spaces such as in the larynx, trachea, and esophagus, as well as through other natural orifices of the body.

SUMMARY

Disclosed are endoscopic staplers and staple removers for medical use, and methods for stapling tissue.

In one aspect, an endoscopic stapler apparatus is disclosed. The apparatus includes a handle including a trigger, an outer shaft coupled to the handle, and an inner shaft with prongs positioned at a distal end of the inner shaft. The endoscopic stapler further includes a hook, wherein the hook and prongs are positioned to capture a staple at a tip of the prongs, wherein a proximal end of the inner shaft is coupled to the trigger, and wherein activation of the trigger causes the prongs to translate away from the handle causing the prongs to bend, close, and deploy the staple.

In another aspect, a method of stapling tissue through an endoscope or natural orifice using an endoscopic stapler is disclosed. The method includes inserting an endoscopic stapler apparatus into an opening of an endoscopic device or into a natural orifice such as the a mouth, a nose or an ear. The method further includes placing a tip of the endoscopic stapler at a location where tissue is to be joined. The method also includes pulling a trigger of the endoscopic stapler toward a handle of the endoscopic stapler, wherein the pulling the trigger causes an inner shaft configured to fit inside an outer shaft and with prongs at a distal end of the inner shaft to extend away from the handle causing the prongs to bend, close and deploy the staple.

In another aspect an endoscopic staple die apparatus is disclosed. The apparatus includes a first die end shaped to preform an endoscopic staple into a predetermined staple shape for an endoscopic stapler, and a second die end shaped to bend a wire section into the predetermined staple shape when pressed together with the first die end.

In another aspect, an endoscopic staple removing apparatus is disclosed. The apparatus includes a handle including a trigger, an outer shaft coupled to the handle, and an inner shaft. The outer shaft has prongs positioned at a distal end of the outer shaft and the inner shaft has a tip at a distal end of the inner shaft, wherein the tip and prongs are positioned to capture a staple between the tip and the prongs, wherein a proximal end of the inner shaft is coupled to the trigger, and wherein activation of the trigger causes the tip to translate away from the handle to cause the tip to bend and remove a closed staple as the tip extends through the prongs.

DETAILED DESCRIPTION

Figure 1:
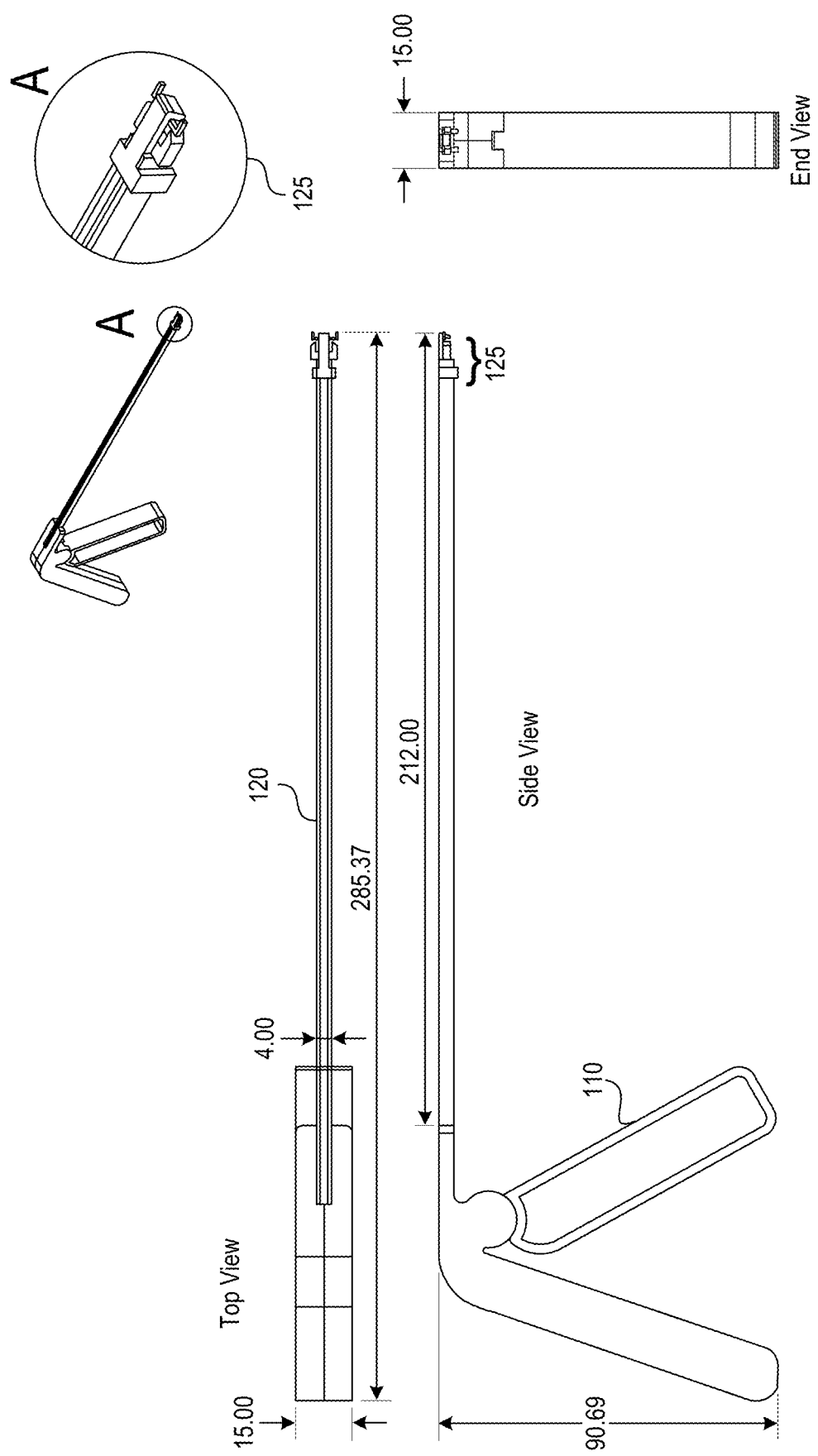
FIG. 1 depicts an example illustration showing a top view, a side view, and an end view of an endoscopic stapler apparatus, in accordance with some example embodiments.

The upper aerodigestive tract includes structures such as the larynx (voice box), trachea and esophagus. These structures are vital to our quality of life and survival. For example, the voice produced by the voice box provides a person with an identity and an ability to communicate with the world around them. The trachea and larynx are critical for respiration and gas exchange necessary for survival. The esophagus provides a safe passage for nutrients into the body. Ailments or trauma may strike any one of these structures in a variety of ways causing scarring and/or dysfunction. Trauma and birth defects may also result in aberrant communications between these structures such as tracheoesophageal fistulae. Cancer and its treatments can also lead to their distortion and dysfunction among other problems.

Treatment of the structures in the upper aerodigestive tract is typically done through transoral endoscopic approaches. For example, a rigid laryngoscope may be used to open the mouth and provide a working channel through which to view and provide treatment. Typically, a working channel of approximately 1-2 centimeters (cm) may be used.

Lasers have aided in providing the ability to cut and remove tissues, but the ability to connect or reconnect and repair tissues through a laryngoscope or rigid endoscope is lacking. Current practice is to use sutures to sew structures together, but this is too cumbersome and difficult through the small channel of a laryngoscope and in other confined spaces.

Disclosed in this document is a small device that can be operated through the small working channel of a laryngoscope, a rigid endoscope, or through a natural orifice such as the mouth, nose, or ear to safely and effectively connect tissues permanently or semi-permanently. The disclosed device can be operated with a single hand to recruit tissue for approximation or for reapproximation of tissue (mucosa) in the upper aerodigestive tract. The disclosed endoscopic stapling device can be used to connect tissues in a stable and semi-permanent or permanent fashion. The device/instrument is thin and long and has an articulating distal end such that the angle of approach can be adjusted as needed. The head, length, width and thickness of the instrument are easily modified for particular applications.

The disclosed device may deploy a single staple at a time. The device may automatically reload another staple after one staple is deployed or each staple may be manually loaded after a staple is deployed. The staples can be made from stainless steel, titanium, or another metal material or may be made from a biodegradable or resorbable material. The staple may be permanent, semi-permanent, or resorbable. Permanent or semi-permanent staples may be removed from the body after healing is complete or sufficiently advanced. A biodegradable or resorbable staple material slowly decays after being deployed in the body such that after a predictable amount of time the staple is naturally eliminated/degraded. For example, a biodegradable staple may be produced from algae based polylactide (PLA). Staples may be supplied as a cartridge with one or more staples which are single use. The staples may be referred to as micro-staples due to their small size. The disclosed device may operate using staples of different sizes, lengths, and/or thicknesses without modification to the device. The staples may be magnetic resonance imaging (MRI) compatible.

The disclosed device allows for easy and efficient trans oral tissue approximation. The disclosed stapling device allows for adjustments to the closing or attachment of tissue by adjusting the position of the staple or even removal and resetting the staple position that is not possible using sutures. The disclosed device may be multi-use or disposable after a single use. The disclosed stapler maintains control and pressure on the staple throughout the stages of staple deployment so that control and grip on staple is maintained throughout the staple deployment.

FIGS. 1-4 and 6 include examples of specific dimensions in millimeters for an apparatus. The dimensions of the various aspects and components of the apparatus may vary from the example values given without affecting following description of the functioning of the apparatus. For example, an apparatus may be longer or shorter than that shown depending on the application. Various of the disclosed components of the endoscopic stapler can be made of plastic, metal such as stainless steel or titanium, or other rigid material including firm plastics. The device may be recyclable.

FIG. 1 depicts an example illustration 100 showing a top view, a side view, and an end view of an endoscopic stapler apparatus, in accordance with some example embodiments. FIG. 1 shows handle 105, trigger 110, and outer shaft 120 of the apparatus. The trigger 110 can be pulled toward the handle 105 which advances prongs away from the handle at the end of an inner shaft (not shown) contained in the outer shaft 120. Advancing the inner shaft causes the prongs to bend the staple captured in the stapler tip 125 around tissue that a physician wishes to staple. The trigger 110 may include a ratcheting mechanism (not shown) that advances deployment of the staple upon ratcheting by pulling the trigger toward the handle. The ratcheting mechanism may be configured so that the trigger is pulled once or multiple times to advance the staple to being fully deployed.

Even though the working channel is very small at 1-2 cm, because the apparatus is narrow, a physician can see down the outer shaft to see where the tip of the endoscopic stapler is located relative to the patient's tissue. To operate the device, a physician may place the outer shaft into the working channel inside a laryngoscope placed in a patient. The tip of the apparatus can be placed at a location where a physician wishes to place a staple. Before deployment, the tips of the staple can be used to grasp and recruit tissue for approximation. Once the tip including the staple are in the correct location, the physician pulls the trigger 110 toward the handle causing the inner shaft to advance toward the distal end of the outer shaft and causing the prongs to bend through and around tissue thereby holding the tissue together via the staple. In some example embodiments, the outer dimensions of the tip may be approximately 3-4 mm (h)×3-5 mm (w) and the length may be between 100 mm and 400 mm with 200 mm being a typical length.

Figure 2:
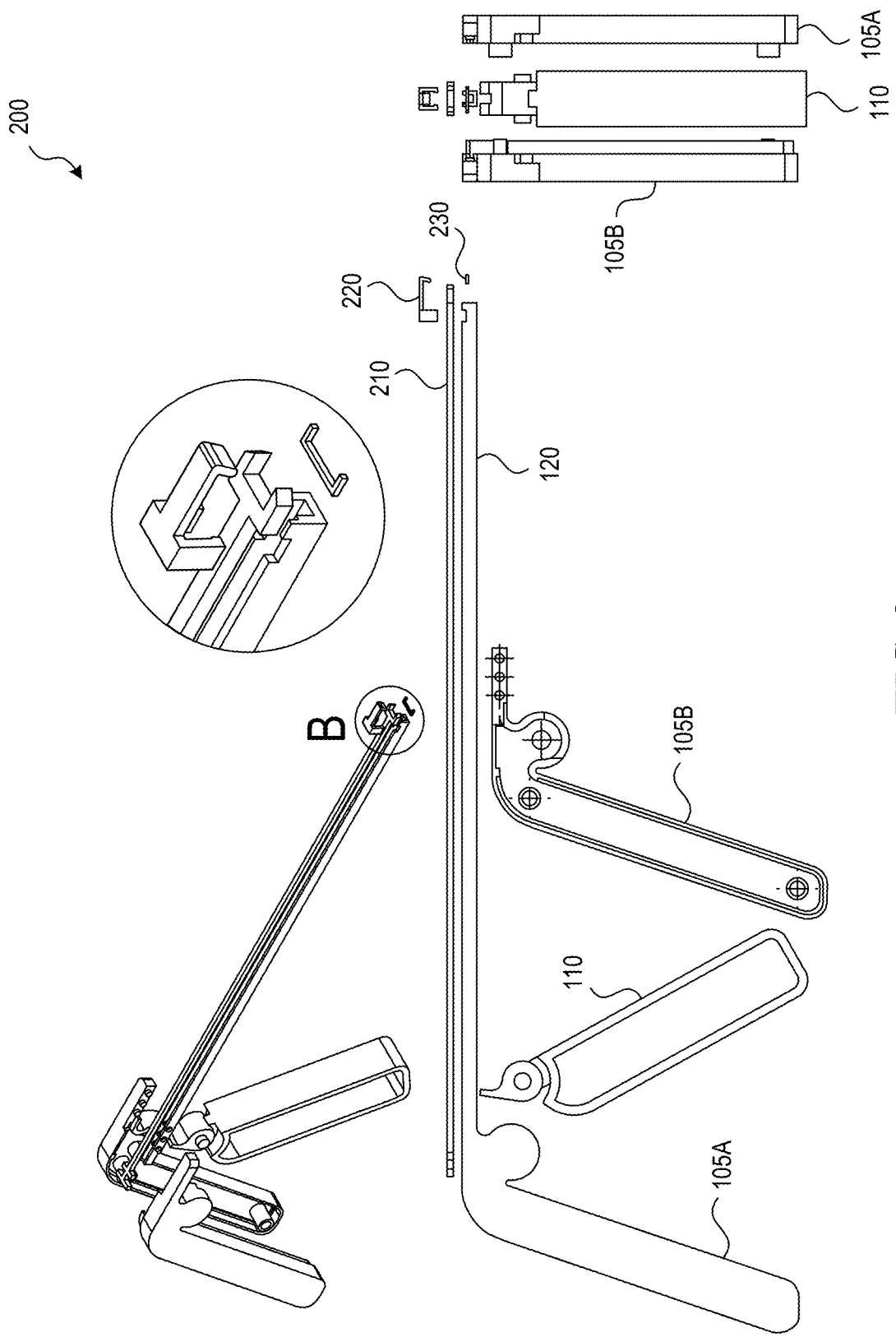
FIG. 2 depicts another illustration showing a side view, an end view, and an exploded view of an endoscopic stapler, in accordance with some example embodiments.

FIG. 2 depicts another illustration 200 showing a side view, an end view, and an exploded view of an endoscopic stapler, in accordance with some example embodiments. In addition to the features shown in FIG. 1, FIG. 2 also shows inner shaft 210 which has prongs 212 at the distal end of the inner shaft and trigger capture extensions 214 at the proximate end of inner shaft 210.

Trigger capture extensions 214 engage with a lobe at a proximate end of trigger 110. When trigger 110 is pulled toward handle 105, the trigger lobe rotates causing the tip of the lobe and the engaged trigger capture extensions to advance away from handle 105 toward the tip of the device.

Staple 230 is held in place at the end of prongs 212 by hook 220. A slight bend at the end of hook 220 captures the staple and holds the staple against the prongs. In the example of FIG. 2, the sides of hook 220 fit on the outside of outer shaft 120, and the top of hook 220 fits into notches in the end of outer shaft 120 so that the top surface of hook 220 is flush with outer shaft 120. In some example embodiments, a spring at the rotation point of the trigger, or at another location in the device, may apply a spring force to hold the trigger extended away from the handle to ensure that the staple is not deployed until a physician applies force to the trigger and the staple does not deploy by accident. The spring force may also be applied by a linear spring applying a spring force along he inner or outer shaft toward the handle tending to prevent deployment of the staple 230.

In the example of FIG. 2, handle 105 includes right half 105A and left half 105B. A series of nubs 240 on right half 105A and left half 105B engage with holes on inner shaft 210 thereby holding the inner shaft and sides of the handle in a fixed position with respect to each other.

Figure 3:
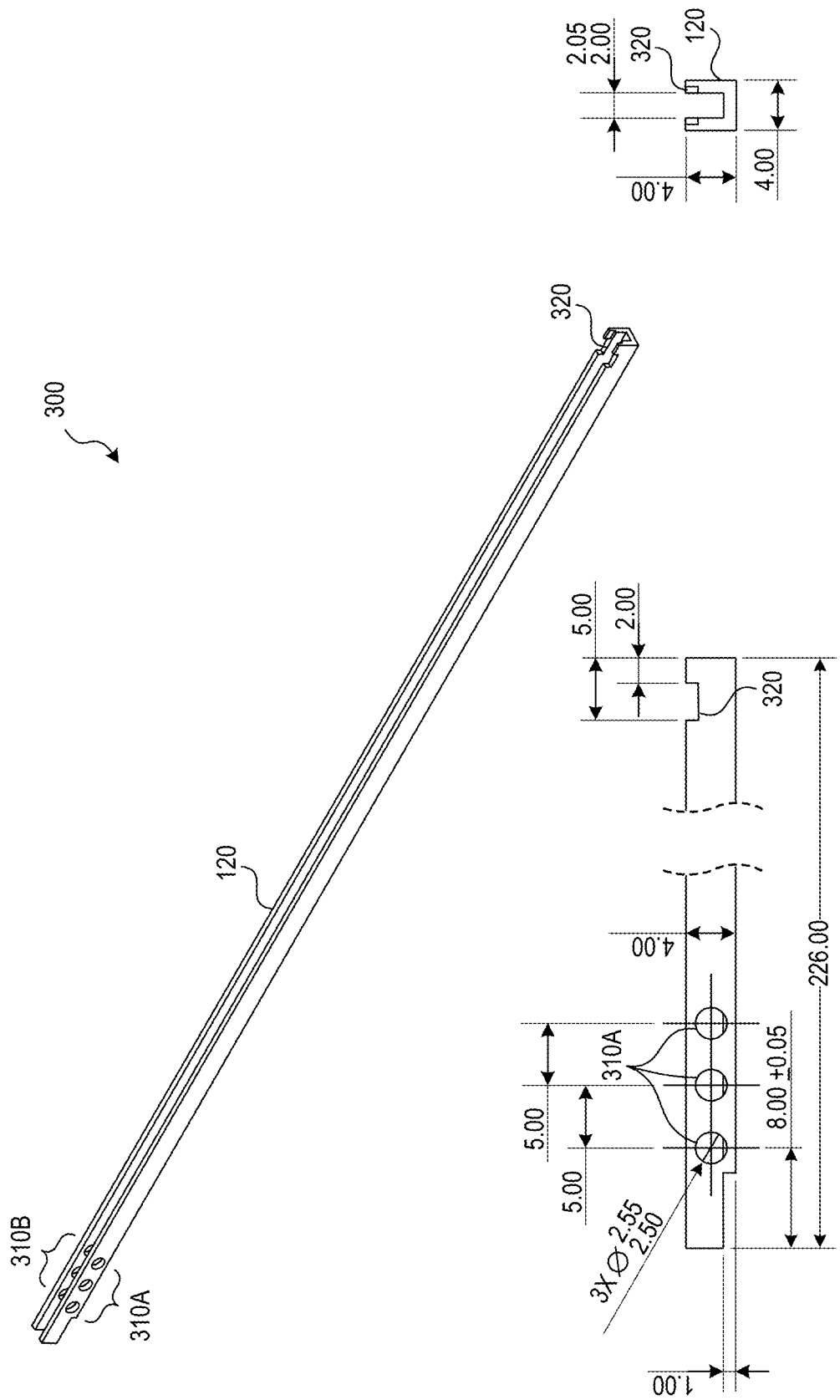
FIG. 3 depicts a detailed view of an outer shaft, in accordance with some example embodiments.

FIG. 3 depicts a detailed view 300 of outer shaft 120, in accordance with some example embodiments. Shown in FIG. 3 are holes 310A that engage with the nubs of handle right half 105A and holes 310B that engage with the nubs of handle left half 310B. Also shown in FIG. 3 are notches 320 that the sides and top surface of prongs 220 fit into.

Figure 4:
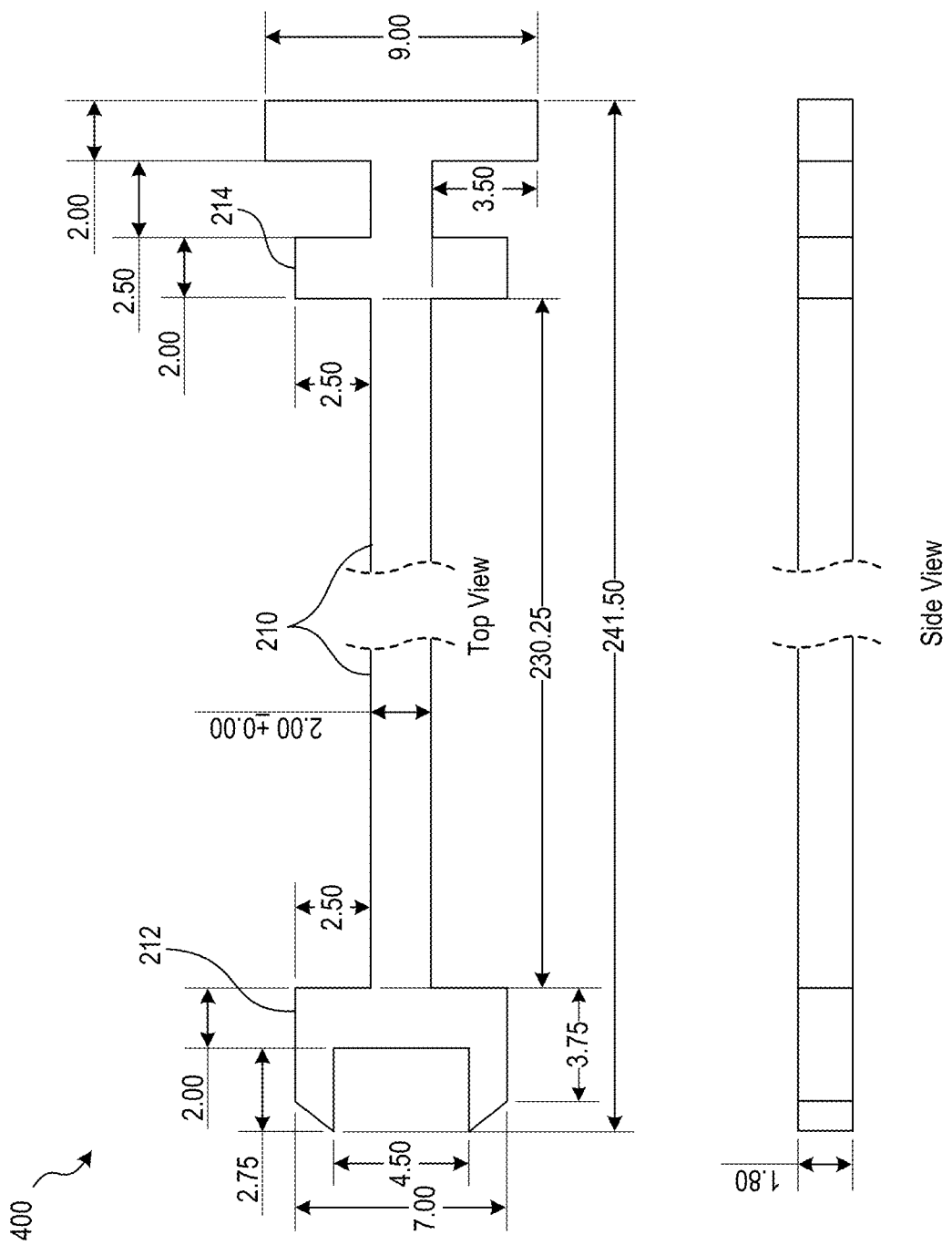
FIG. 4 depicts a detailed view of an inner shaft, in accordance with some example embodiments.

FIG. 4 depicts a detailed view 400 of an inner shaft 210, in accordance with some example embodiments. Shown are prongs 212 and trigger capture extensions 214. In the example of FIG. 4, trigger capture extensions 214 have an "H" shape with one side of the "H" shorter than the other. Other trigger capture shapes can be used also. In the example of FIG. 4, each prong tip of prongs 212 is angled making the inner most edge of each prong somewhat pointed. Other prong tip shapes can also be used such as prong tips that are pointed at the center of each prong instead of the inner edge, or pointed at the outer edge of each prong. Also, in some embodiments, the prongs may not be pointed.

Figure 5:
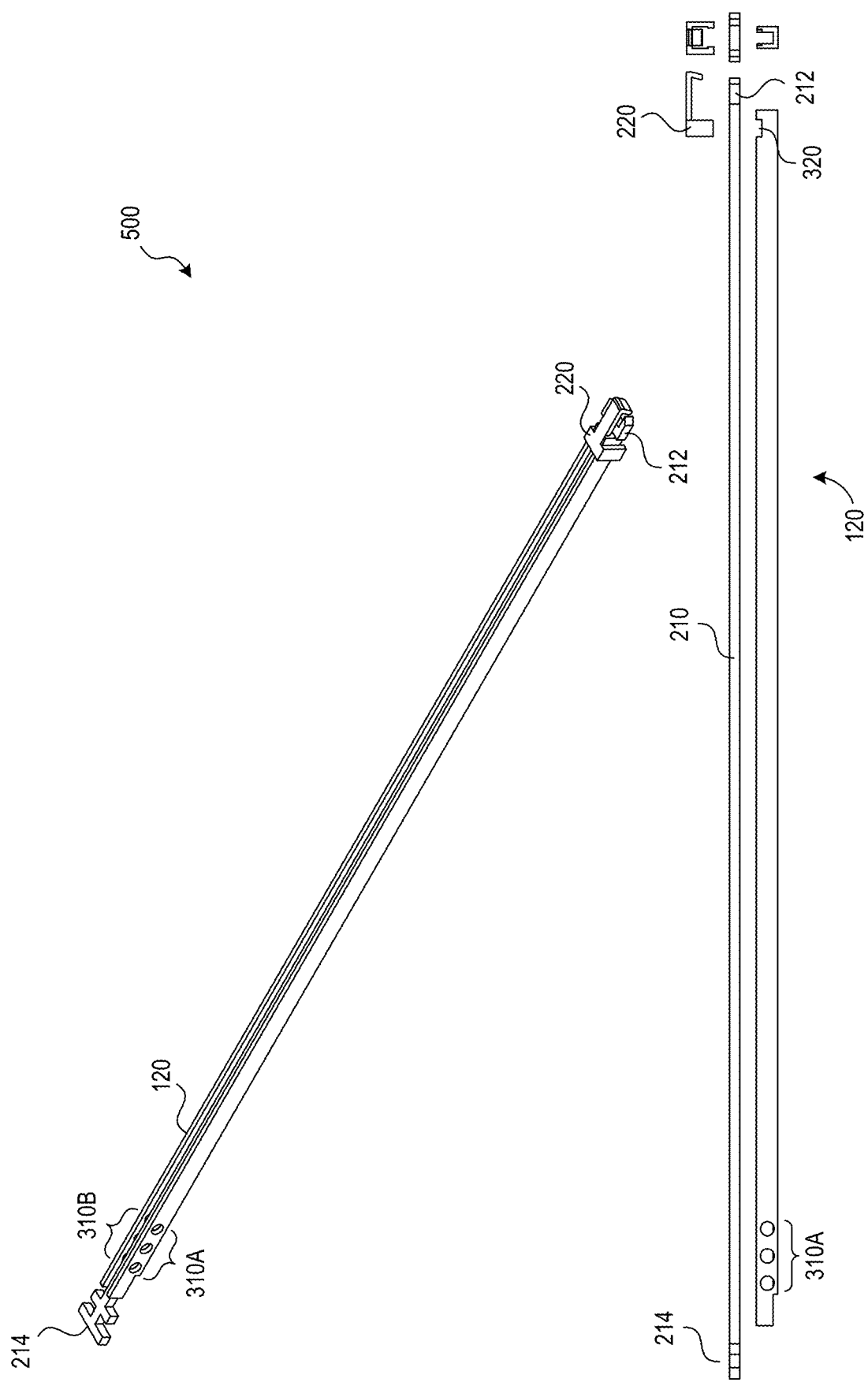
FIG. 5 depicts a detailed view of inner shaft placed inside an outer shaft, in accordance with some example embodiments.

FIG. 5 depicts a detailed view 500 of inner shaft 210 placed inside outer shaft 120, in accordance with some example embodiments. Shown in FIG. 5 are prongs 212, hook 220, trigger capture extensions 214, holes 310A/B, outer shaft 120.

In some of the example embodiments described above, the inner and outer shafts are made of a rigid material such as metal or plastic. As described above and in the figures, the inner and outer shafts may be rectangular in cross sectional shape. In some embodiments, at least a portion of the inner and outer shafts may be round in cross sectional shape. For example, the inner and outer shafts may be rectangular at the distal end where prongs 212 are located, and may transition to being round from the prongs to the proximate end at the handle and trigger. In other example embodiments, the inner and outer shafts may be flexible so that the distal end where the prongs are located may be bent up/down/right/left to allow the apparatus to be placed through a curved passageway and/or to adjust the angle of approach of the staple to the patient's tissue. In some example embodiments, a round flexible outer shaft may be similar to a typical adjustable lamp. In other embodiments, different rectangular or round inner and outer shafts may be made of rigid material with a fixed bend at some point along the length. For example, at a predetermined length from the tip, the inner and outer shafts may be bent by 5 or 10 degrees. Different angles at different locations may be produced and the physician can select the appropriate bend for a particular patient and procedure. In some example embodiments, the tip may be rotatable.

The disclosed endoscopic stapler may be disposable after use on a patient or may be reusable after proper cleaning. The stapler may be manufactured for single use or multi-use and may be retrofittable with different tips, lengths, and angles of shafts.

Figure 6:
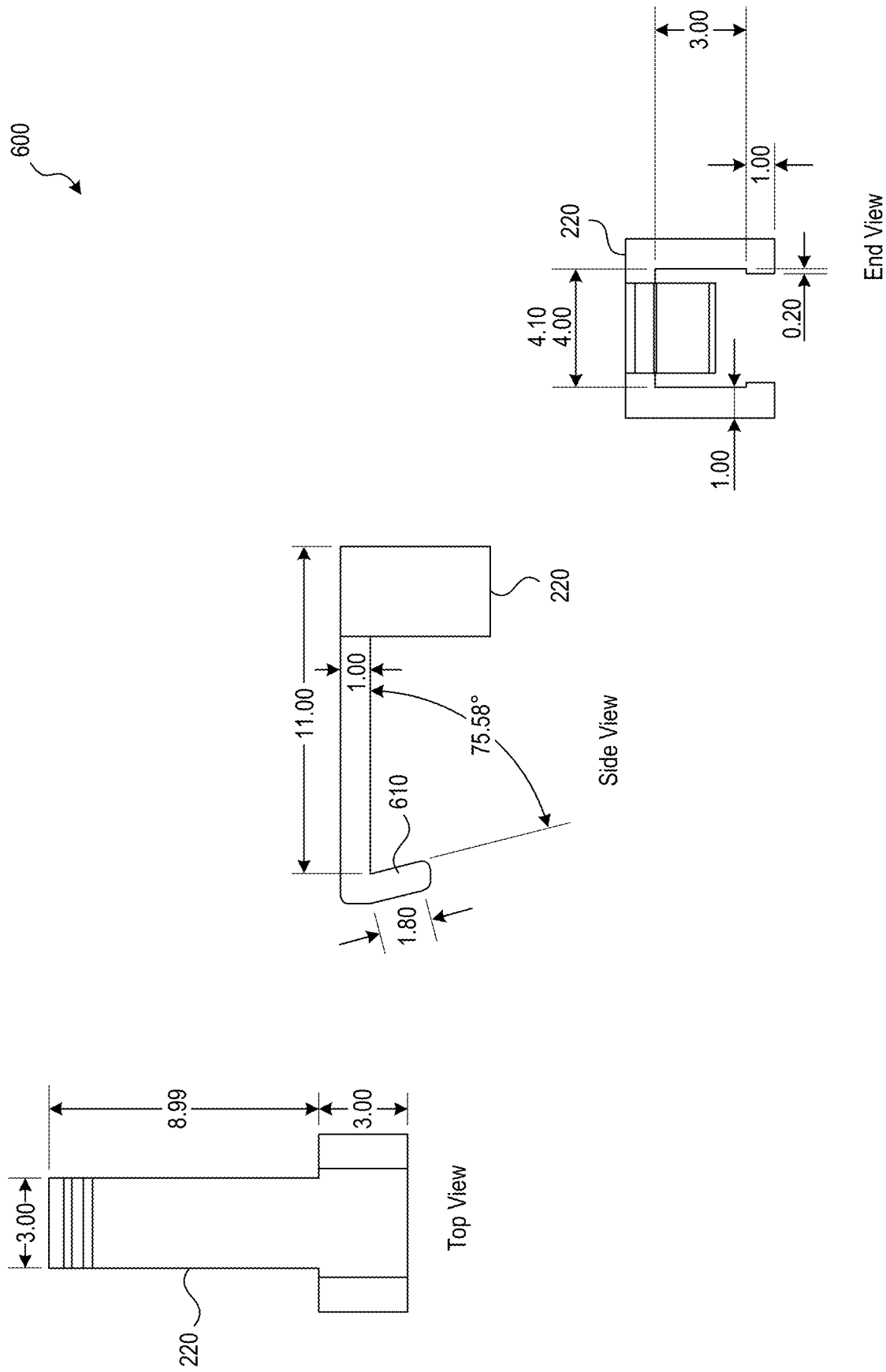
FIG. 6 depicts at an end view, a side view, and an end view of hook, in accordance with some example embodiments.

FIG. 6 depicts an end view, a side view, and an end view of hook 220, in accordance with some example embodiments. Shown at 610 is angled tip 610 of hook 220 as described above. The angled tip aids holding the staple in position until deployment.

Figure 7:
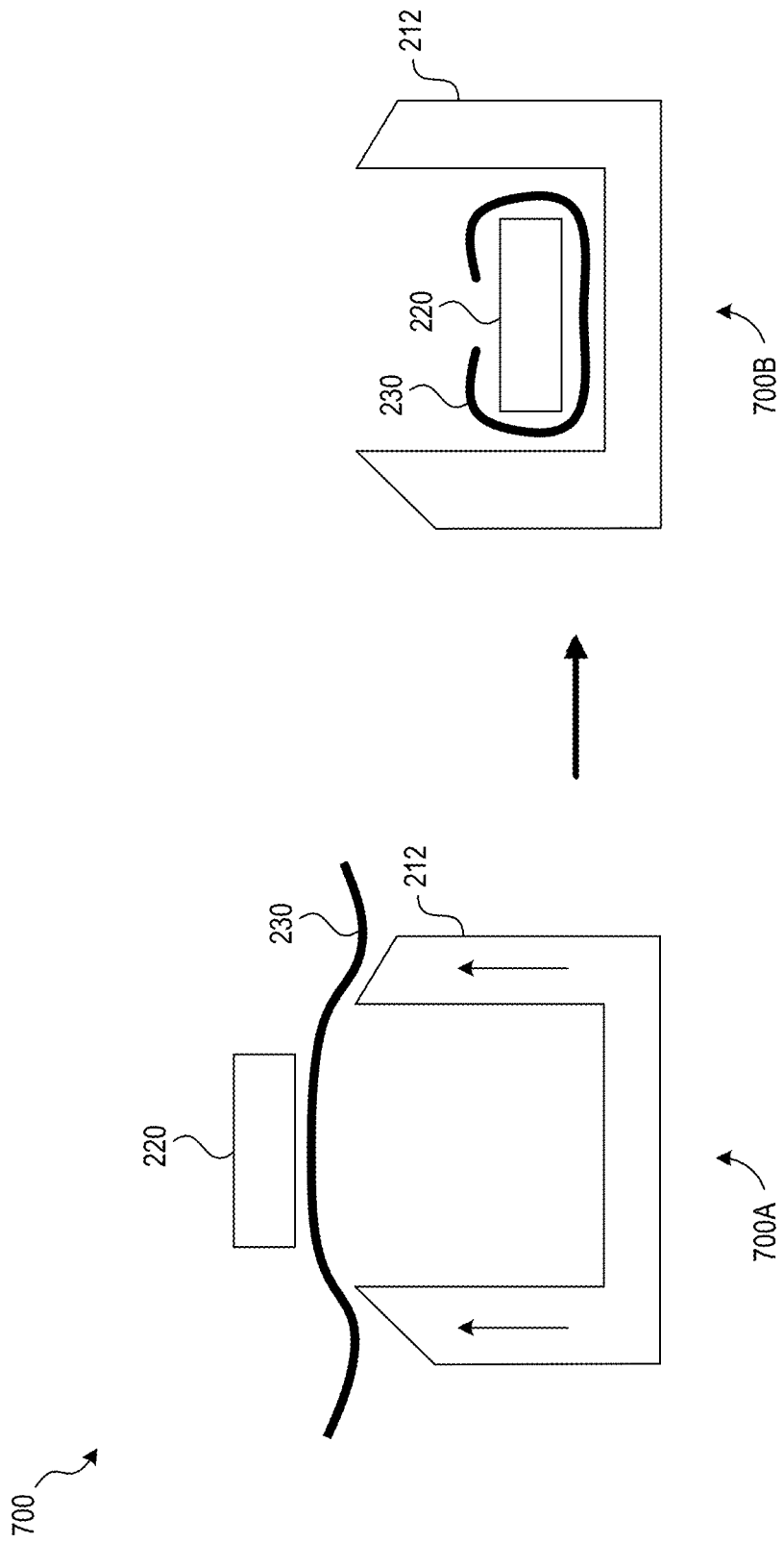
FIG. 7 depicts an illustration showing the staple shape before deployment and after being bent by deployment, in accordance with some example embodiments.

FIG. 7 depicts an illustration showing the staple 230 being bent from before deployment by pulling the device trigger to after deployment. At 700A, the staple is shown before deployment with staple 230 being held into position by hook 220 and prongs 212. At deployment, the prongs move forward toward the hook 220. As the prongs 212 move forward, staple 230 is bent around hook 220. As the staple 230 is bent, the staple pierces and/or captures tissue (not shown) that is held together by staple 230 after the hook 220 is retracted from the tissue site.

Figure 8:
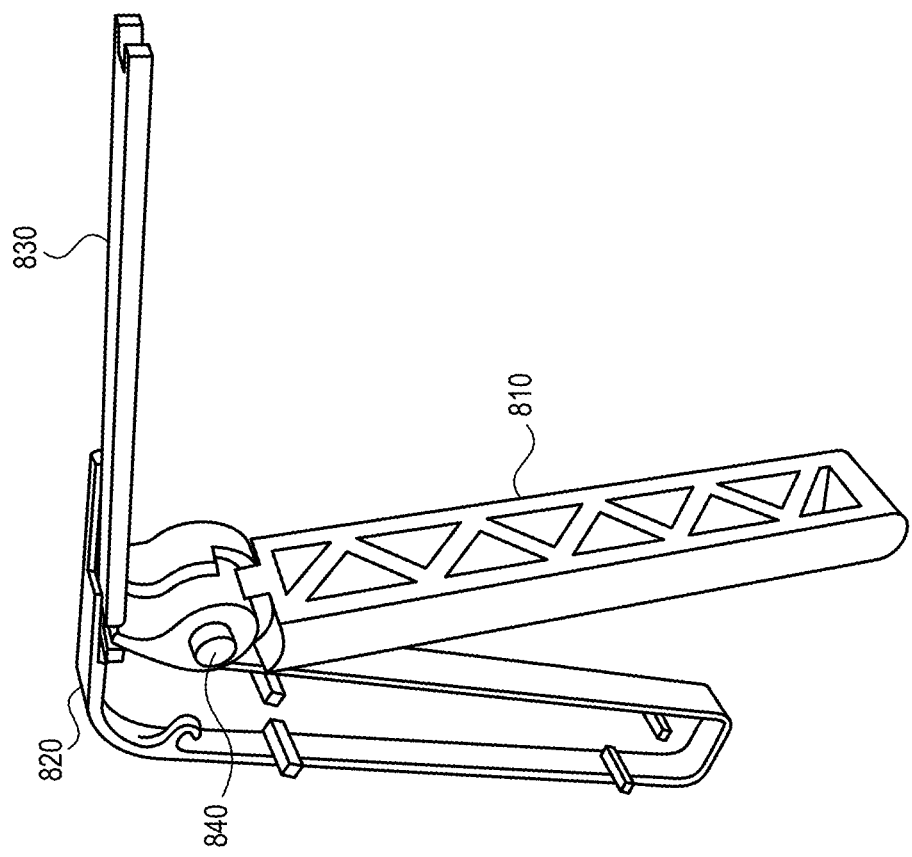
FIG. 8 shows examples of a trigger, one side of a handle, and an outer shaft.
Figure 8:
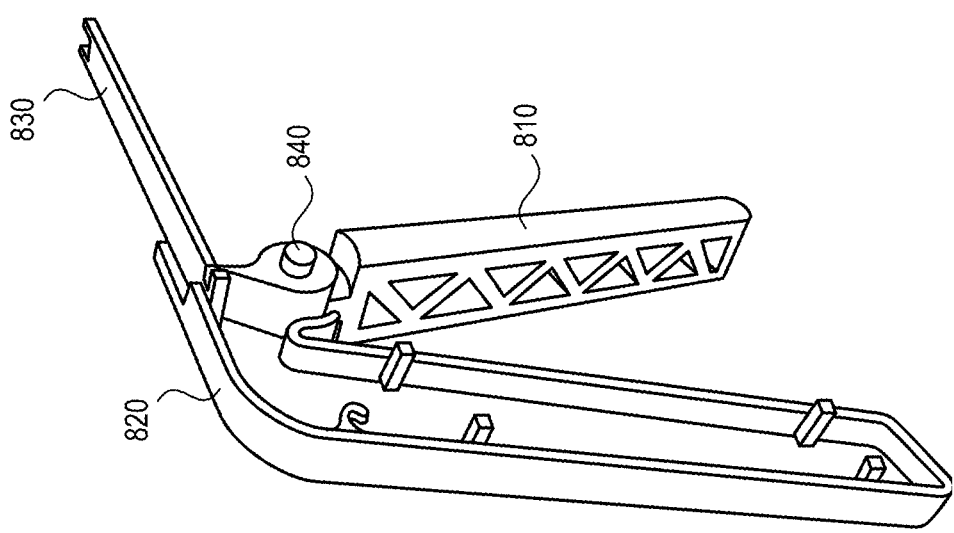

FIG. 8 shows examples of portions of a stapler apparatus including the trigger 810, one side of the handle 820, and the outer shaft 830. During actuation of the apparatus, the trigger 810 rotates toward the handle 820 about pivot 840.

Figure 9:
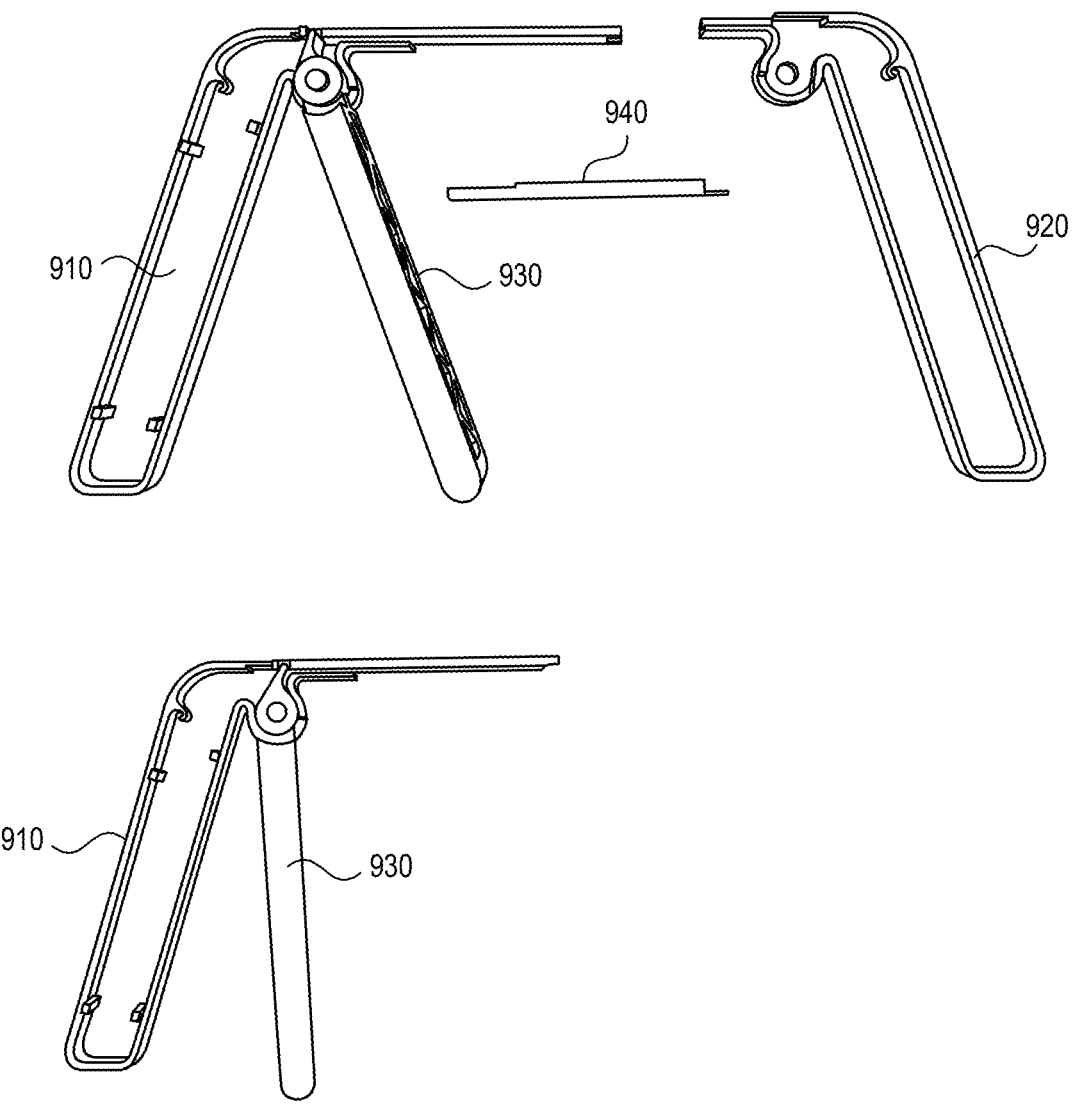
FIG. 9 shows examples of a right-side handle, a left side handle, and an outer shaft.

FIG. 9 shows examples of portions of the apparatus including the right-side handle 920, the left-side handle 910, and an outer shaft 940.

Figure 10:
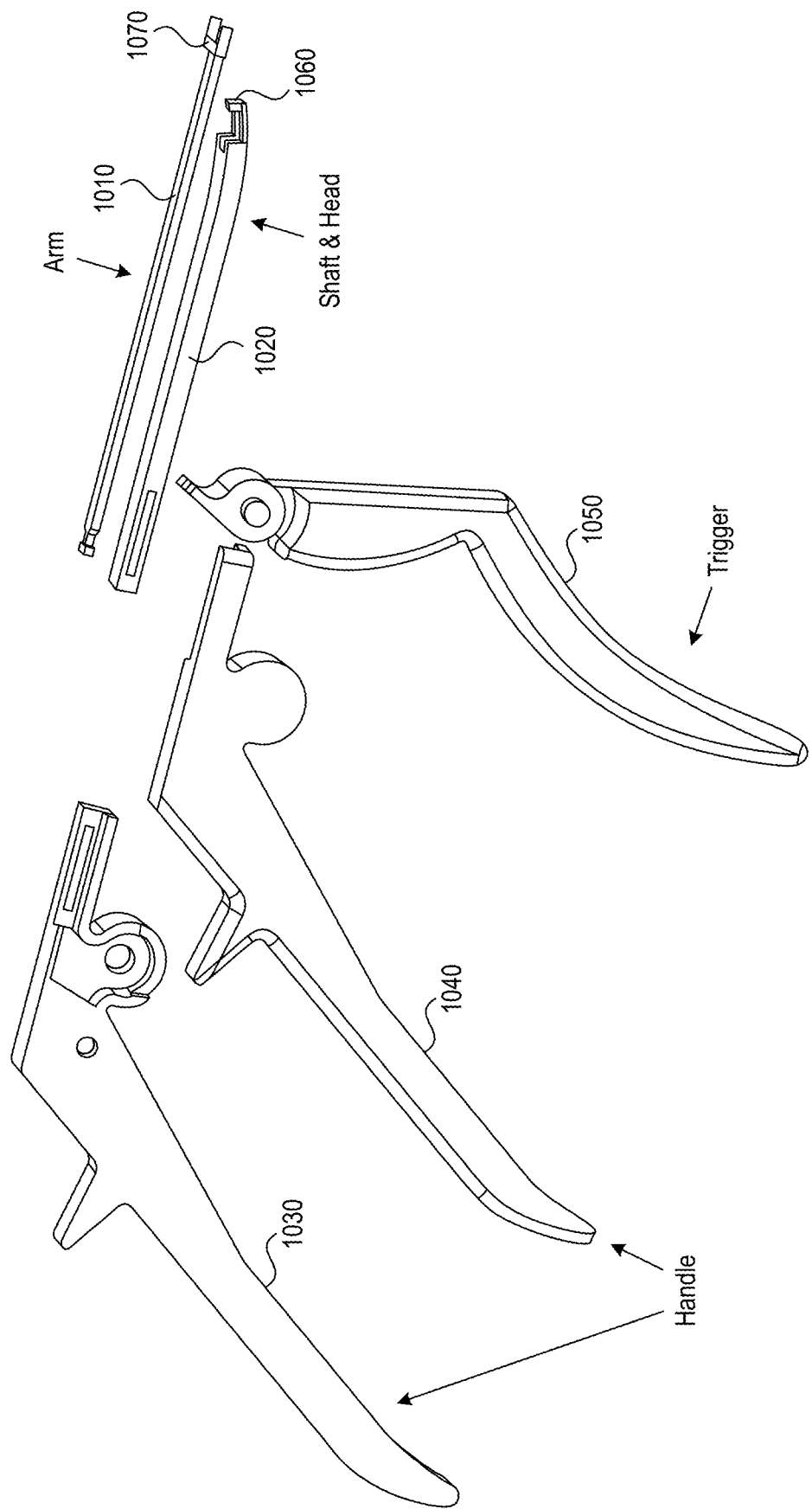
FIG. 10 shows an exploded view of a stapler, in accordance with some example embodiments.

FIG. 10 shows an exploded view of a stapler, in accordance with some example embodiments. The embodiment in FIG. 10 has a shortened inner shaft 1010 and outer shaft 1020 compared to some other embodiments. For example, a typical length of the inner and outer shafts in the FIG. 10 embodiment may be between 60 mm and 150 mm with a typical length of about 100 mm. This is compared to other embodiments that have inner and outer shaft lengths between 100 mm and 400 mm with 200 mm being a typical length. Also shown in FIG. 10 are a left side handle 1030, right side handle 1040, and trigger 1050.

The handle including left-side handle 1030 and right-side handle 1040 combine together with trigger 1050. The handle and trigger of the stapler are designed to be comfortable to hold and actuate while delivering enough torque to the anterior end 1060 to bend the staples to their final shape. The stapler handle provides a feel to medical personnel that is familiar and delivers sufficient force to the anterior end 1060 while being easy and comfortable to use.

In some embodiments, the outer shaft 1020 of the stapler has an elongated mostly enclosed body with approximately a 5 degree bend at the head 1060 (the distal end of the outer shaft). The bend may be made with smaller or larger angles. The bent head allows an operator to have a line of sight view of the stapler tip before and during use. The upward bend may be adjustable on the apparatus before use and the bend may be set to various angles depending on the procedure being performed. The apparatus maintains the set angle. The correct angle may depend on the orifice of the medical procedure and available space and viewing limitations caused by other instruments used in the procedure.

The inner shaft 1010 of the stapler slides through the outer shaft 1020 and interacts with the staple at the head 1060 as described above. The inner shaft 1010 and outer shaft 1020 are customizable to any desired length.

Figure 11:
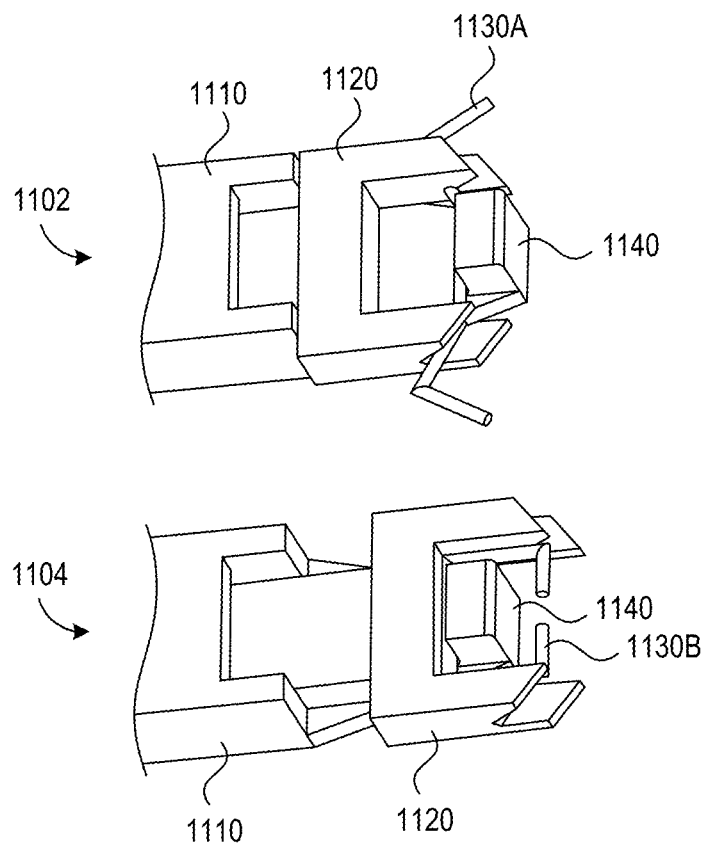
FIG. 11 shows an example of a stapler head.

At the head 1060 of the stapler, the pronged end 1070 of the inner shaft pushes a staple loaded in the head 1060 around the end of the outer shaft as further detailed in FIG. 11. The notched shape of the prongs 1070 prevents unwanted rotation in the staple during the application. The distance between the prongs in combination with the width of the outer shaft end determines the final staple shape. The shape of the final staple can be adjusted by the shape of the head and/or prongs and by the extent that the prongs are extended during application of the staple.

FIG. 11 shows an example of a stapler head. A staple 1130 is loaded at a distal end 1140 of the outer shaft 1110 with and prongs 1130 at the end of the inner shaft 1120. Shown at 1102 is the stapler head before trigger actuation where the staple 1130A is in pre-installation shape and at 1104 is the stapler head after trigger actuation where the staple 1130B is in a post-installation shape. When used in practice, the stapler head is placed near tissue that the operator wishes to staple, the trigger pulled to actuate the stapler causing the staple to change shape from 1130A to 1130B with the ends of the staple piercing through and holding the tissue in place in accordance with the staple 1130B shape.

Figure 12:
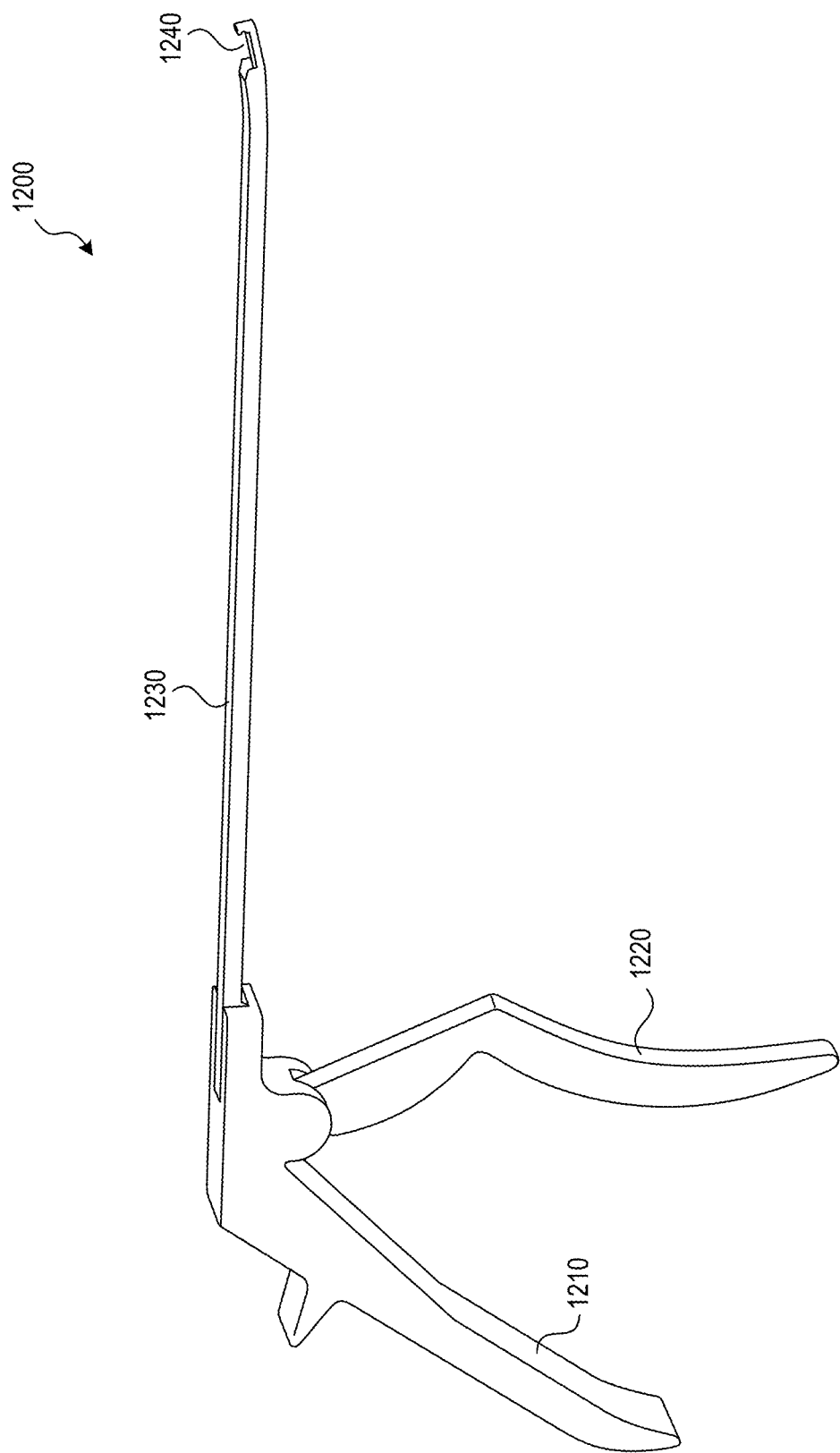
FIG. 12 shows an example of an endoscopic stapler, in accordance with some example embodiments.

FIG. 12 shows an example of an endoscopic stapler 1200, in accordance with some example embodiments. Shown are handle 1210, trigger 1220, and outer shaft 1230 with distal end 1240. The stapler can be actuated by pulling the trigger 1220 toward handle 1210.

Figure 13:
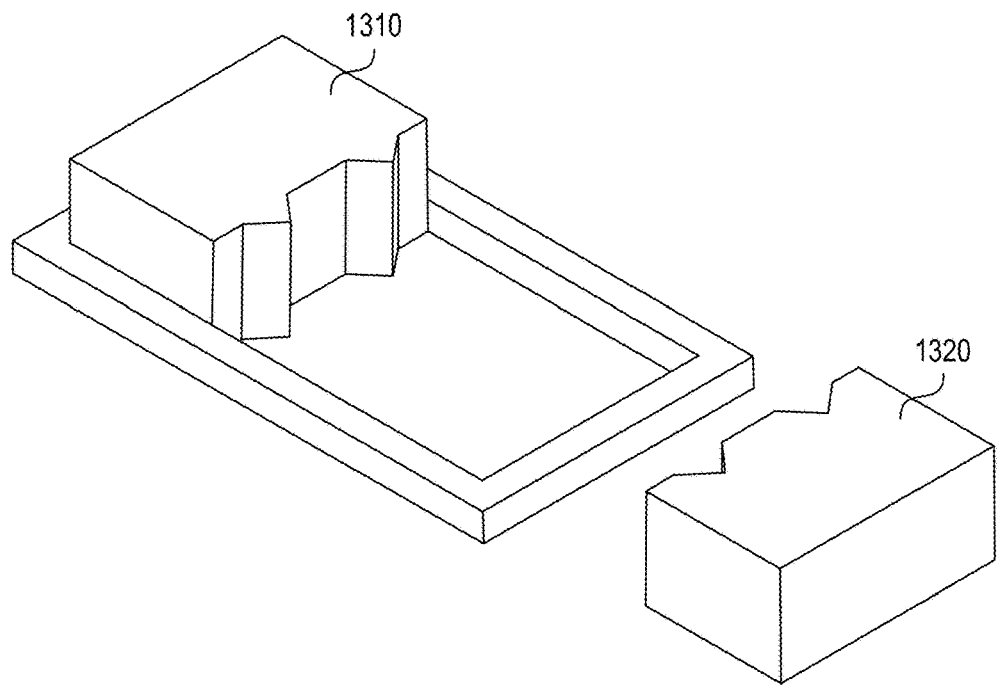
FIGS. 13 and 14 shows an example of a staple die that can be used to produce staples for some embodiments of the disclosed endoscopic staplers and staple removers.
Figure 14:
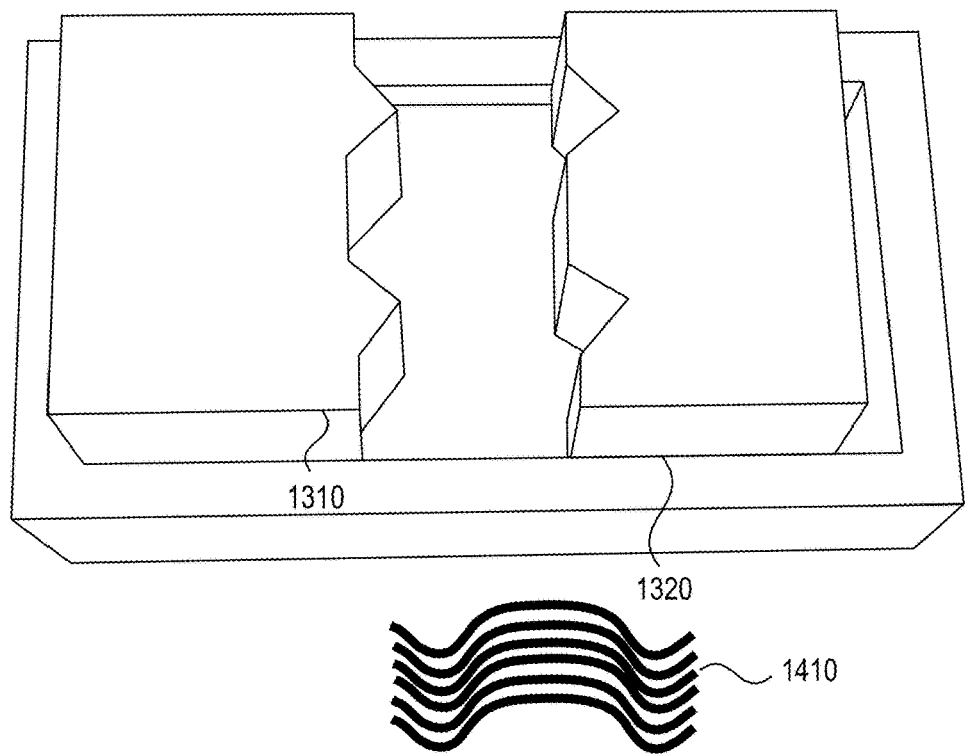

FIGS. 13 and 14 show an example of a staple die that can be used to produce staples for some embodiments of the endoscopic staplers and staple removers disclosed in this patent document. An example die has two ends 1310 and 1320. When a section of staple stock or a material such as a small metal rod, wire, or other material is placed between the ends 1310 and 1320 followed by pressing the ends together, a staple in a shape determined by the die is produced. The section of staple stock can be made from wire of various gauges and/or materials. Multiple staples may be produced at a time by stacking multiple sections of staple stock on top of one another followed by pressing the ends 1310 and 1320 together. For example, six staples may be produced together as shown at 1410. Use of the die ensures that the shape of the produced staples is of consistent shape resulting in consistent stapler performance.

Figure 15:
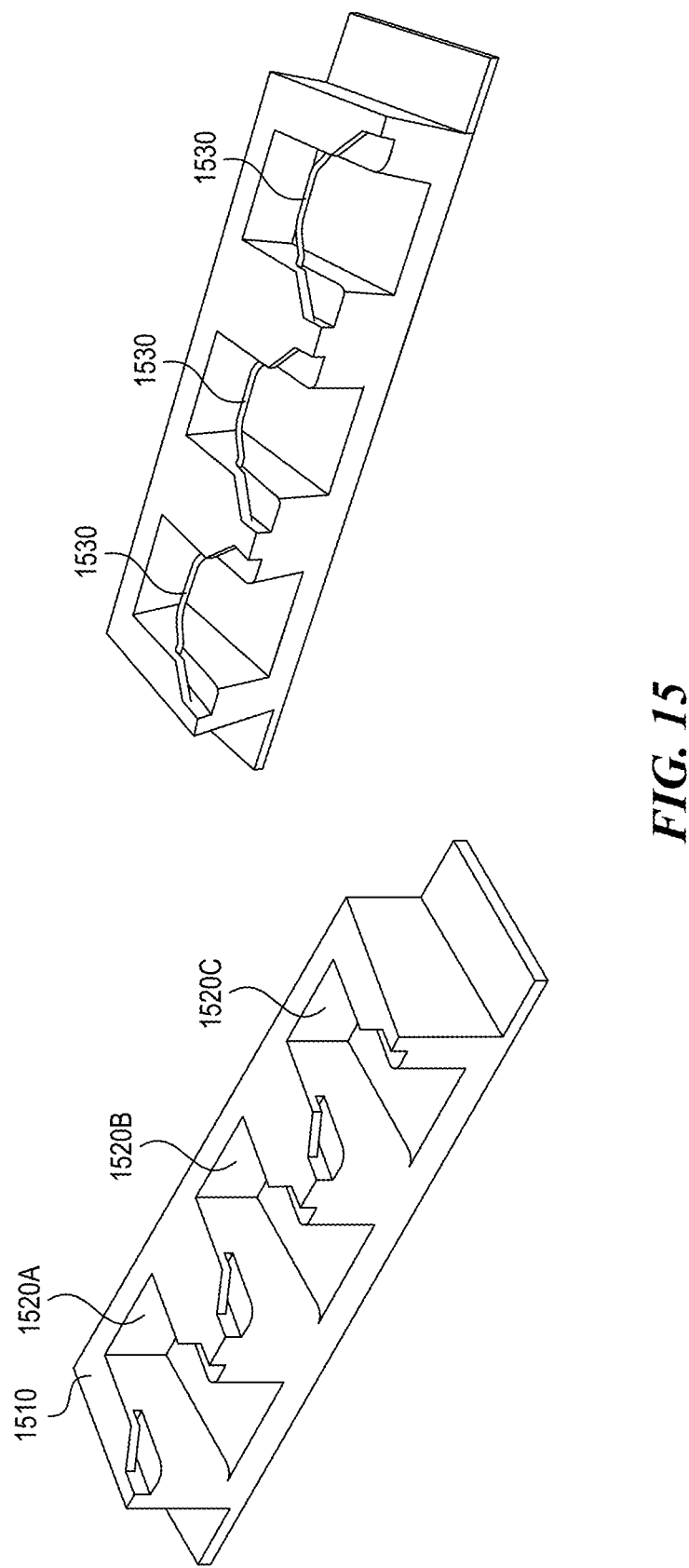
FIG. 15 shows an example of a staple cartridge.

FIG. 15 shows an example of a staple cartridge 1510. Some example embodiments, the endoscopic stapler holds and deploys a single staple at a time. The external staple cartridge 1510 reduces the time needed to reload the stapler during a procedure while eliminating the need to touch staples in order to load them into the stapler. The staple cartridge makes the using the stapler in a medical procedure faster, safer, and more sanitary. The cartridge is modular and can be expanded to have any number of staple sites in the cartridge 1510. In the example of 1510, three staple sites are shown 1520A, 1520B, and 1520C. Each staple site accommodates a staple 1530.

Figure 16:
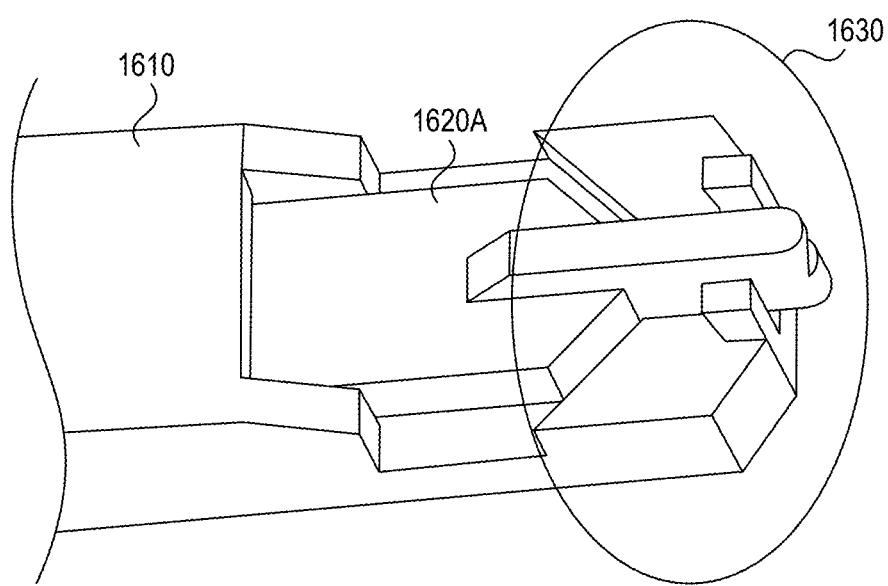
FIGS. 16 and 17 show an example of a staple remover.
Figure 17:
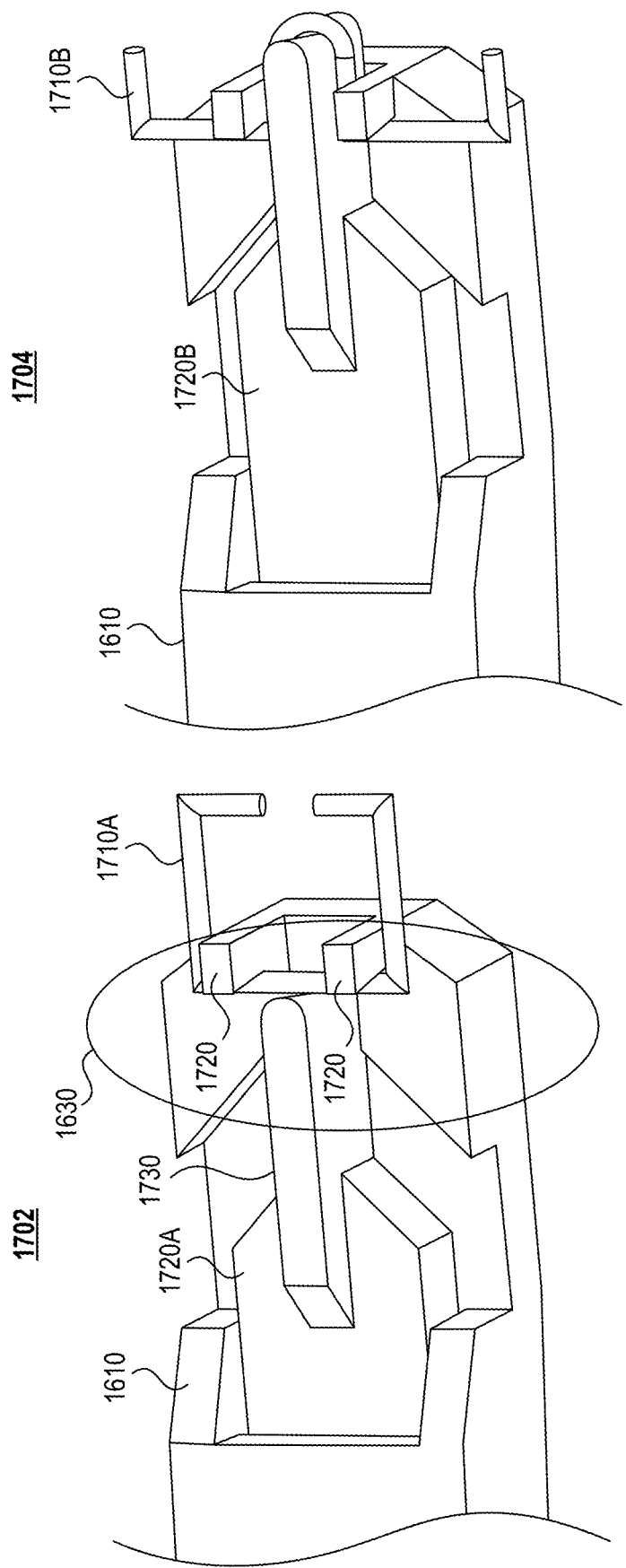

FIGS. 16 and 17 show an example of a staple remover. In the example shown in FIGS. 16 and 17, the staple remover has a design that is similar to the endoscopic stapler disclosed in this patent document having an outer shaft 1610 and an inner shaft 1620. The staple remover has a different head 1630 which bends the staples from an initial position that is closed to a final position that is open. FIG. 16 shows the staple remover with the inner shaft extended away from the handle and toward the head 1630 corresponding to the position of the inner shaft with respect to the outer shafts after a staple has been removed.

FIG. 17 shows the staple remover 1702 before the trigger has been actuated to remove the staple 1710A and the staple remover 1704 after the trigger has been actuated to remove the staple. At 1702, the inner shaft 1720A is retracted toward the handle. The head of the staple remover 1630 is placed on the staple 1710A to be removed so that the staple is positioned between the distal end of the inner shaft 1720A and prongs 1720 at the distal end of the outer shaft 1610. At 1704, the inner shaft has been actuated by the trigger to move the inner shaft away from the handle and toward the distal end of the outer shaft 1610. As the inner shaft 1720A extends away from the handle due to the trigger, tip 1730 bends the staple 1710A by pressing the staple against the prongs 1720. As the tip 1730 extends further, the staple continues to bend against the prongs 1720 to the final position of the inner shaft resulting in a final removed staple 1710B. After removal, the staple 1710B is gripped between the inner shaft 1720B and outer shaft 1610 until the tool has been removed from the body orifice and the trigger is released.

Figure 18:
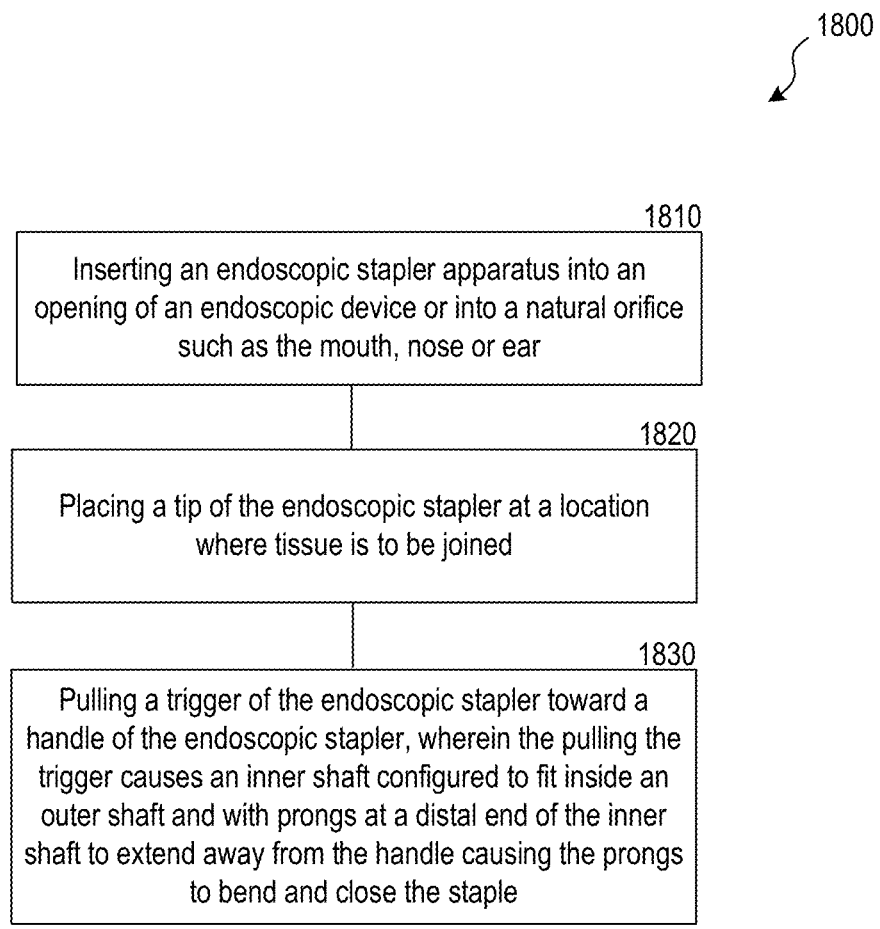
FIG. 18 depicts a method, in accordance with some example embodiments.

FIG. 18 depicts a method 1800, in accordance with some example embodiments. At 1810, the method includes inserting an endoscopic stapler apparatus such as the endoscopic stapler described above into an opening of an endoscopic device or directly into a natural orifice such as the mouth, nose or ear. At 1820, the method includes placing a tip of the endoscopic stapler at a location where tissue is to be joined. For example, the tip may be placed inside a laryngoscope in the upper aerodigestive tract of a patient at a location where tissue is to be joined. At 1830, the method includes pulling a trigger of the endoscopic stapler toward a handle of the endoscopic stapler, wherein the pulling the trigger causes an inner shaft configured to fit inside an outer shaft and with prongs at a distal end of the inner shaft to extend away from the handle causing the prongs to bend and close the staple.

The above disclosed technology can be implemented in various configurations. Some examples of implementations are detailed in the clauses below.

Clause 1. An endoscopic stapler apparatus, comprising: a handle including a trigger; an outer shaft coupled to the handle; an inner shaft with prongs positioned at a distal end of the inner shaft; and a hook, wherein the hook and prongs are positioned to capture a loaded staple at a tip of the prongs, wherein a proximal end of the inner shaft is coupled to the trigger, and wherein activation of the trigger causes the prongs to translate away from the handle causing the prongs to bend, close, and deploy the staple.

Clause 2. The endoscopic stapler apparatus of clause 1, wherein the proximal end of the inner shaft comprises a first interlocking portion structured to interlock with a second interlocking portion at a proximal end of the trigger, wherein the second interlocking portion interlocked with the first interlocking portion is configured to translate together in a direction toward the distal end of the outer shaft when the trigger is pulled toward the handle.

Clause 3. The endoscopic stapler apparatus of clause 1, wherein the inner shaft and the outer shaft are colinear.

Clause 4. The endoscopic stapler apparatus of clause 1, wherein the inner shaft and the outer shaft are bendable together to cause the distal end of the inner shaft and the outer shaft to change an angle of approach between tissue to be stapled and the staple.

Clause 5. The endoscopic stapler apparatus of clause 4, wherein the inner shaft and the outer shaft remain in a bent position after being bent, and wherein the bent position is reconfigurable to different positions.

Clause 6. The endoscopic stapler apparatus of clause 1, wherein the inner shaft is configured to fit inside and be captured by the outer shaft.

Clause 7. The endoscopic stapler apparatus of clause 1, wherein a length of the inner shaft is between 6 cm and 40 cm.

Clause 8. The endoscopic stapler apparatus of clause 1, wherein a cross-section of the distal end of the endoscopic stapler is about 5 mm by 5 mm.

Clause 9. The endoscopic stapler apparatus of clause 1, wherein the staple comprises stainless steel, a titanium material, metal alloy, plastic or polymer or a biodegradable material.

Clause 10. The endoscopic stapler apparatus of clause 1, wherein a lateral cross-sectional shape of the inner shaft and the outer shaft is rectangular.

Clause 11. The endoscopic stapler apparatus of clause 1, wherein a lateral cross-sectional shape of at least a portion of the inner shaft and the outer shaft is circular.

Clause 12. The endoscopic stapler apparatus of clause 1, wherein the trigger includes a ratchet mechanism requiring one or multiple pulls of the trigger to deploy the staple Clause 13. A method of stapling tissue through an endoscope or natural orifice using an endoscopic stapler, the method comprising: inserting an endoscopic stapler apparatus into an opening of an endoscopic device or into a natural orifice such as a mouth, a nose or an ear; placing a tip of the endoscopic stapler at a location where tissue is to be joined; and pulling a trigger of the endoscopic stapler toward a handle of the endoscopic stapler, wherein the pulling the trigger causes an inner shaft configured to fit inside an outer shaft and with prongs at a distal end of the inner shaft to extend away from the handle causing the prongs to bend, close and deploy the staple.

Clause 14. The method of clause 13, further comprising bending, before inserting the endoscopic stapler into the opening, the tip of the endoscopic stapler to change the angle of approach into the tissue.

Clause 15. The method of clause 14, wherein the inner shaft and the outer shaft remain in a bent position after the bending, and wherein the bent position is reconfigurable to different positions.

Clause 16. The method of clause 13, wherein a length of the inner shaft is between 10 cm and 40 cm.

Clause 17. The method of clause 13, wherein a cross-section of the distal end of the endoscopic stapler is about 5 mm by 5 mm.

Clause 18. The method of clause 13, wherein the staple comprises stainless steel, a titanium material, metal alloy, plastic or polymer or a biodegradable material Clause 19. An endoscopic staple die apparatus, comprising: a first die end shaped to preform an endoscopic staple into a predetermined staple shape for an endoscopic stapler; and a second die end shaped to bend a wire section into the predetermined staple shape when pressed together with the first die end.

Clause 20. The endoscopic staple die apparatus of clause 19, wherein the first die end and the second die end are configured to bend multiple endoscopic staples at a time.

Clause 21. An endoscopic staple removing apparatus, comprising: a handle including a trigger; an outer shaft coupled to the handle, wherein the outer shaft has prongs positioned at a distal end of the outer shaft; and an inner shaft with a tip at a distal end of the inner shaft, wherein the tip and prongs are positioned to capture a staple between the tip and the prongs, wherein a proximal end of the inner shaft is coupled to the trigger, and wherein activation of the trigger causes the tip to translate away from the handle to cause the tip to bend and remove a closed staple as the tip extends through the prongs.

Clause 22. The endoscopic staple removing apparatus of clause 21, wherein the proximal end of the inner shaft comprises a first interlocking portion structured to interlock with a second interlocking portion at a proximal end of the trigger, wherein the second interlocking portion interlocked with the first interlocking portion is configured to translate together in a direction toward the distal end of the outer shaft when the trigger is pulled toward the handle.

Clause 23. The endoscopic stapler apparatus of clause 21, wherein the inner shaft and the outer shaft are colinear.

Clause 24. The endoscopic stapler apparatus of clause 21, wherein the inner shaft and the outer shaft are bendable together causing the distal end of the inner shaft and the outer shaft to change an angle of approach between tissue to be stapled and the staple.

Clause 25. The endoscopic stapler apparatus of clause 24, wherein the inner shaft and the outer shaft remain in a bent position after being bent, and wherein the bent position is reconfigurable to different positions.

Although a few variations have been described in detail above, other modifications or additions are possible. In particular, further features and/or variations may be provided in addition to those set forth herein. Moreover, the example embodiments described above may be directed to various combinations and subcombinations of the disclosed features and/or combinations and subcombinations of several further features disclosed above. In addition, the logic flow depicted in the accompanying figures and/or described herein does not require the particular order shown, or sequential order, to achieve desirable results. Other embodiments may be within the scope of the following claims.

Similarly, while elements are depicted in the drawings in a particular order, this should not be understood as requiring that the elements be assembled or performed in the particular order shown or in sequential order, or that all illustrated operations be performed, to achieve desirable results. Moreover, the separation of various elements in the embodiments described in this patent document should not be understood as requiring such separation in all embodiments.

Only a few implementations and examples are described and other implementations, enhancements and variations can be made based on what is described and illustrated in this patent document.

What is claimed is:

1. An endoscopic stapler apparatus, comprising:
    a handle including a trigger and a top surface with a flat section;
    a flexible outer shaft coupled to the handle and comprising a flat top surface and a distal end, wherein a portion of the distal end of the flexible outer shaft is angled with respect to a longitudinal axis of the flexible outer shaft, wherein the flat top surface of the flexible outer shaft and the top surface of the flat section of the handle are coplanar with respect to each other;
    a flexible inner shaft with prongs positioned at a distal end of the flexible inner shaft and trigger capture extensions positioned at a proximal end of the flexible inner shaft, wherein the flexible inner shaft is positioned inside the flexible outer shaft, wherein the flexible inner shaft and the flexible outer shaft are dimensioned to allow maneuverability of the apparatus through passageways of a natural orifice comprising an ear, a nose, or a mouth; and
    a hook, wherein the hook and prongs are positioned to capture a staple at a tip of the prongs, wherein the proximal end of the flexible inner shaft is coupled to the trigger, and wherein activation of the trigger causes the trigger capture extensions to advance away from the handle causing the prongs to translate away from the handle to bend, close, and deploy the staple,
    wherein the top surface of the flat section of the handle, the flat top surface of the flexible outer shaft, and the portion of the distal end of the flexible outer shaft that is angled with respect to the longitudinal axis of the flexible outer shaft provide a line of sight of the staple along a longitudinal axis of the apparatus that is not obstructed when the apparatus is inserted into the natural orifice and is being actuated.

2. The endoscopic stapler apparatus of claim 1, wherein the proximal end of the flexible inner shaft comprises a first interlocking portion structured to interlock with a second interlocking portion at a proximal end of the trigger, wherein the second interlocking portion interlocked with the first interlocking portion is configured to translate together in a direction toward the distal end of the flexible outer shaft when the trigger is pulled toward the handle.

3. The endoscopic stapler apparatus of claim 1, wherein the flexible inner shaft is positioned inside the flexible outer shaft such that the flexible inner shaft and the flexible outer shaft are substantially parallel to one another.

4. The endoscopic stapler apparatus of claim 1, wherein the flexible inner shaft and the flexible outer shaft are bendable together to cause the distal end of the flexible inner shaft and the flexible outer shaft to change an angle of approach between tissue to be stapled and the staple.

5. The endoscopic stapler apparatus of claim 4, wherein the flexible inner shaft and the flexible outer shaft remain in a bent position after being bent, and wherein the bent position is reconfigurable to different positions.

6. The endoscopic stapler apparatus of claim 1, wherein the flexible inner shaft is configured to fit inside and be captured by the flexible outer shaft.

7. The endoscopic stapler apparatus of claim 1, wherein a length of the flexible inner shaft is between 6 cm and 40 cm.

8. The endoscopic stapler apparatus of claim 1, wherein a cross-section of the distal end of the endoscopic stapler apparatus is about 5 mm by 5 mm.

9. The endoscopic stapler apparatus of claim 1, wherein the staple comprises stainless steel, a titanium material, metal alloy, plastic or polymer or a biodegradable material.

10. The endoscopic stapler apparatus of claim 1, wherein a lateral cross-sectional shape of the flexible inner shaft and the flexible outer shaft is rectangular.

11. The endoscopic stapler apparatus of claim 1, wherein a lateral cross-sectional shape of at least a portion of the flexible inner shaft and the flexible outer shaft is circular.

12. The endoscopic stapler apparatus of claim 1, wherein the trigger includes a ratchet mechanism requiring one or multiple pulls of the trigger to deploy the staple.

13. A method of stapling tissue through an endoscope or natural orifice using an endoscopic stapler, the method comprising:
 inserting an endoscopic stapler into an opening of an endoscopic device or into a natural orifice comprising a mouth, a nose or an ear, wherein the endoscopic stapler comprises:
  a handle including a trigger and a top surface with a flat section,
  a flexible outer shaft coupled to the handle and comprising a flat top surface and a distal end, wherein a portion of the distal end of the flexible outer shaft is angled with respect to a longitudinal axis of the flexible outer shaft, wherein the flat top surface of the flexible outer shaft and the top surface of the flat section of the handle are coplanar with respect to each other, and
  a flexible inner shaft with prongs positioned at a distal end of the flexible inner shaft, wherein the flexible inner shaft is positioned inside the flexible outer shaft;
 placing a tip of the endoscopic stapler at a location where tissue is to be joined; and
 pulling a trigger of the endoscopic stapler toward a handle of the endoscopic stapler such that trigger capture extensions coupled to the trigger become engaged and advance away from the handle upon the pulling the trigger, wherein the pulling the trigger causes the flexible inner shaft with the prongs at the distal end of the flexible inner shaft to extend away from the handle causing the prongs to bend, close and deploy a staple,
 wherein the top surface of the flat section of the handle, the flat top surface of the flexible outer shaft, and the portion of the distal end of the flexible outer shaft that is angled with respect to the longitudinal axis of the flexible outer shaft provide a line of sight of the staple along a longitudinal axis of the endoscopic stapler that is not obstructed when the endoscopic stapler is inserted into the opening of the endoscopic device or into the natural orifice and the endoscopic stapler is being actuated.

14. The method of claim 13, further comprising:
 bending, before inserting the endoscopic stapler into the opening, the tip of the endoscopic stapler to change an angle of approach into the tissue.

15. The method of claim 14, wherein the flexible inner shaft and the flexible outer shaft remain in a bent position after the bending, and wherein the bent position is reconfigurable to different positions.

16. The method of claim 13, wherein a length of the flexible inner shaft is between 10 cm and 40 cm.

17. The method of claim 13, wherein a cross-section of the distal end of the endoscopic stapler is about 5 mm by 5 mm.

18. The method of claim 13, wherein the staple comprises stainless steel, a titanium material, metal alloy, plastic or polymer or a biodegradable material.

19. An endoscopic staple removing apparatus, comprising:
 a handle including a trigger and a top surface with a flat section;
 a flexible outer shaft coupled to the handle and comprising a flat top surface, wherein the outer shaft has prongs positioned at a distal end of the flexible outer shaft, wherein a portion of the distal end of the flexible outer shaft is angled with respect to a longitudinal axis of the flexible outer shaft, wherein the flat top surface of the flexible outer shaft and the top surface of the flat section of the handle are coplanar with respect to each other, and
 flexible inner shaft with a tip at a distal end of the flexible inner shaft, wherein the tip and prongs are positioned to capture a staple between a rounded portion of the tip and the prongs, wherein a proximal end of the flexible inner shaft is coupled to the trigger, and wherein activation of the trigger causes the tip to translate away from the handle to cause the tip to bend a closed staple around the rounded portion of the tip such that the closed staple is shaped by the rounded portion and remove the closed staple as the tip extends through the prongs,
 wherein the flexible inner shaft is positioned inside the flexible outer shaft, wherein the flexible inner shaft and the flexible outer shaft are dimensioned to allow maneuverability of the apparatus through passageways of a natural orifice comprising an ear, a nose, or a mouth,
 wherein the top surface of the flat section of the handle, the flat top surface of the flexible outer shaft, and the portion of the distal end of the flexible outer shaft that is angled with respect to the longitudinal axis of the flexible outer shaft provide a line of sight of the staple along a longitudinal axis of the apparatus that is not obstructed when the apparatus is inserted into natural orifice and is being actuated.

20. The endoscopic staple removing apparatus of claim 19, wherein the proximal end of the flexible inner shaft comprises a first interlocking portion structured to interlock with a second interlocking portion at a proximal end of the trigger, wherein the second interlocking portion interlocked with the first interlocking portion is configured to translate together in a direction toward the distal end of the flexible outer shaft when the trigger is pulled toward the handle.

21. The endoscopic staple removing apparatus of claim 19, wherein the flexible inner shaft is positioned inside the flexible outer shaft such that the flexible inner shaft and the flexible outer shaft are substantially parallel to one another.

22. The endoscopic staple removing apparatus of claim 19, wherein the flexible inner shaft and the flexible outer shaft are bendable together causing the distal end of the flexible inner shaft and the flexible outer shaft to change an angle of approach between tissue to be stapled and the staple.

23. The endoscopic staple removing apparatus of claim 22, wherein the flexible inner shaft and the flexible outer shaft remain in a bent position after being bent, and wherein the bent position is reconfigurable to different positions.

* * * * *